(12) United States Patent
Salorinne

(10) Patent No.: US 11,696,721 B2
(45) Date of Patent: Jul. 11, 2023

(54) ARRANGEMENT FOR PROACTIVELY NOTIFYING AND ADVISING USERS IN TERMS OF POTENTIALLY HEALTH-AFFECTING LOCATION-RELATED PHENOMENA, RELATED METHOD AND COMPUTER PROGRAM

(71) Applicant: Kamu Health OY, Helsinki (FI)

(72) Inventor: Seppo Salorinne, Helsinki (FI)

(73) Assignee: MEDIKRO OY, Kuopio (FI)

( * ) Notice: Subject to any disclaimer, the term of this patent is extended or adjusted under 35 U.S.C. 154(b) by 424 days.

(21) Appl. No.: 16/645,002

(22) PCT Filed: Sep. 6, 2018

(86) PCT No.: PCT/FI2018/050630
§ 371 (c)(1),
(2) Date: Mar. 6, 2020

(87) PCT Pub. No.: WO2019/048739
PCT Pub. Date: Mar. 14, 2019

(65) Prior Publication Data
US 2020/0281518 A1    Sep. 10, 2020

(30) Foreign Application Priority Data

Sep. 6, 2017 (FI) .................................... 20175793

(51) Int. Cl.
*A61B 5/00* (2006.01)
*G16H 10/60* (2018.01)
*A61B 5/08* (2006.01)

(52) U.S. Cl.
CPC ............ *A61B 5/411* (2013.01); *A61B 5/0022* (2013.01); *A61B 5/08* (2013.01); *A61B 5/7275* (2013.01); *A61B 5/7475* (2013.01); *G16H 10/60* (2018.01)

(58) Field of Classification Search
CPC ............................ A61B 5/7257; A61B 5/1118
(Continued)

(56) References Cited

U.S. PATENT DOCUMENTS 8,807,131 B1    8/2014 Tunnell et al.
9,075,909 B2    7/2015 Almogy et al.
(Continued)

FOREIGN PATENT DOCUMENTS

CA        2840871 A1        1/2013
WO     2015160830 A1      10/2015
(Continued)

OTHER PUBLICATIONS

European Search Report Application No. 18853603.1 dated Apr. 12, 2021.
(Continued)

*Primary Examiner* — Fabricio R Murillo Garcia
(74) *Attorney, Agent, or Firm* — Thomas | Horstemeyer, LLP

(57) ABSTRACT

The present disclosure presents at least one communication interface for prediction of data related to health conditions, wherein the at least one communication interface is configured to receive health-related data, preferably comprising measurement data, from a first user device of a first user, associated with a first time and a first location. The at least one communication interface additionally comprises at least one processor configured to utilize said received health-related data to generate predictive data to be indicated to a second user device of a second user associated with a second time and a second location.

9 Claims, 2 Drawing Sheets

(58) Field of Classification Search
USPC .......................................................... 600/556
See application file for complete search history.

(56) References Cited

U.S. PATENT DOCUMENTS

| | | | |
|---|---|---|---|
| 2008/0294019 A1* | 11/2008 | Tran | G16H 40/63 |
| | | | 600/301 |
| 2011/0077758 A1* | 3/2011 | Tran | G16H 40/67 |
| | | | 700/282 |
| 2013/0317379 A1 | 11/2013 | Brimer et al. | |
| 2013/0318027 A1* | 11/2013 | Almogy | G16H 50/20 |
| | | | 706/52 |
| 2014/0052465 A1 | 2/2014 | Madan et al. | |
| 2015/0213194 A1 | 7/2015 | Wolf et al. | |
| 2015/0242509 A1 | 8/2015 | Pall et al. | |
| 2016/0015324 A1 | 1/2016 | Du Bois | |
| 2016/0151021 A1* | 6/2016 | Feng | A61B 5/7282 |
| | | | 600/484 |
| 2017/0109493 A1 | 4/2017 | Hogg et al. | |
| 2017/0161617 A1 | 6/2017 | Avegliano et al. | |

FOREIGN PATENT DOCUMENTS

| | | | |
|---|---|---|---|
| WO | 2016172614 A1 | 10/2016 | |
| WO | 2017194447 A1 | 11/2017 | |

OTHER PUBLICATIONS

International Search Report issued for application PCT/FI2018/050630, dated Feb. 15, 2019.
Written Opinion issued for application PCT/FI2018/050630, dated Feb. 19, 2019.

* cited by examiner

ARRANGEMENT FOR PROACTIVELY NOTIFYING AND ADVISING USERS IN TERMS OF POTENTIALLY HEALTH-AFFECTING LOCATION-RELATED PHENOMENA, RELATED METHOD AND COMPUTER PROGRAM

This application is a National Stage of International Application No. PCT/FI2018/050630, filed Sep. 6, 2018, which claims benefit of Finland Application No. 20175793 filed Sep. 6, 2017, which are hereby incorporated herein by reference in its entireties.

TECHNICAL FIELD OF THE INVENTION

The invention is related to methods to aid in health conditions. More specifically, the invention is related to an arrangement and method for prediction of health-related data associated with a time and a location.

BACKGROUND OF THE INVENTION

A variety of factors influence the condition of a person suffering from a respiratory disease such as asthma or chronic obstructive pulmonary disease (COPD), many of these factors being environment-related. Such factors may include e.g. allergens, smoke, dust, particulates, or pollutants.

It would thus be beneficial for a person to be aware of e.g. environmental conditions that may influence his/her condition in order to prepare for or prevent exacerbations. There is technology available, for example, to warn patients if it is known that a certain environmental trigger potentially affecting their condition is generally present at their location. However, mere presence of a certain potentially detrimental condition does not necessarily affect all persons equally or at all. Yet, taking the necessary measures by a certain person to minimize the effect may be challenging if not impossible, when the condition is already on at the location of the person.

SUMMARY OF THE INVENTION

A purpose of the invention is to alleviate at least some of the problems relating to the known prior art. In accordance with one aspect of the present invention, an arrangement typically of substantially electronic type is provided for prediction of data related to health conditions, wherein the arrangement comprises at least one communication interface configured to receive health-related data, preferably comprising measurement data, from a first user device of a first user, associated with a first time, wherein the first time preferably substantially corresponds to or comprises the instant or interval of measuring and/or recording the data, and a first location, wherein the first location preferably corresponds to or comprises the measurement location.

The arrangement additionally comprises at least one processor configured to utilize said received health-related data to generate predictive data related to a second user and related/to be indicated to a second user device in the possession of or generally associated with the second user, and further related to a second time and a second location, wherein the second time preferably corresponds to a later instant or interval (e.g. future instant/interval) than the first time so that the received health-related data associated with the first user corresponding to the first instant is already available and may be readily utilized having regard to and by the second user relative to the second location, which may be at a distance from the first location. The second location may be an estimated future location of the second user, if not the current location, for instance.

According to one other aspect, a method is provided for prediction of data related to health conditions wherein the method comprises: providing at least one first user device, providing at least one second user device, receiving health-related data from the at least one first user device associated with a first time and a first location, and generating predictive data related to the at least one second user device associated with a second time and a second location.

Having regard to the utility of the present invention, according to an embodiment, an arrangement may predict data affecting the health of e.g. an asthma or COPD patient, or a user suffering from some other medical such as a respiratory or specifically a pulmonary condition. The data may be related to e.g. environmental conditions.

Utilizing embodiments of the invention, a user of the arrangement may thus become aware of for example environmental conditions (e.g. circumstances) affecting his/her health status associated with a time instant or interval in the future and a location in which the user is situated at the present time and/or e.g. a location in which the user will or might be situated at said future time or close to said future time. Preferably, the user may select a time and/or location of interest for obtaining a related prediction. The selection may be provided via a user interface (UI) of the arrangement, which may comprise e.g. a graphical UI accessible via a user device, such as a smartphone, wearable electronics, or a personal computer. Alternatively or additionally, the arrangement may be configured to estimate a future location of the user by extrapolating a future location based on past location(s) and/or relying on e.g. available calendar data that may be preferably automatically retrieved or received from a digital repository stored locally in a user device or in a network entity such as a server or service implemented by a number of servers, for instance.

Accordingly, the arrangement may inform a user of the conditions and/or the arrangement may inform a user of the possible repercussions of the conditions, which concern e.g. a future time instant and location as discussed herein. E.g., a prediction involving a health status or a symptom may be indicated. Also the severity of e.g. the symptom may be predicted and indicated to a user.

In some embodiments, the arrangement may send a notification to a user device if a number of selected conditions are fulfilled and/or if certain values associated with received and/or generated data exceed or remain below predetermined threshold values. The notification may be of alert nature e.g. in cases wherein the conditions may negatively affect or specifically worsen the health status of a user associated with the user device.

In the aforementioned circumstances concerning when a notification may be sent to a user device, in one embodiment the arrangement may also additionally or alternatively send recommendations or suggested actions to be taken by a user to an associated user device. These may be combined in the notification or transmitted separately therefrom, for instance.

In some embodiments, the arrangement may be configured to receive data from an external system such as the one of a healthcare provider. The arrangement may in other embodiments also send data thereto.

Utilizing various embodiments of the present invention, large amounts of patient (user) data may be applied in order to generate personalized predictive data including e.g. proactive notifications, advantageously gaining benefits from gathering data from a large amount of users/patients in order to make more effective predictions than that which are seen in the prior art.

In various embodiments, the arrangement may be thereby configured to obtain and store, in a memory thereof (e.g. in a database or other data structure), user data, such as demographics or other user profile data and health data, indicative of e.g. at least one element selected from the group consisting of: age, gender, health condition or status (e.g. disease(s) and/or symptom(s)), medical record or diagnosis data, measurement data such as health-related measurement data, historical measurement data, spirometry data, air-flow or specifically respiratory measurement data, location data, location history data, current location, future location data, calendar data, future travel data, and predictive data.

The memory may refer to one or more memory chips, for example. Optionally the memory is integrated within the processing unit. In addition to user data, the memory may store control data such as a computer program for controlling the hosting device (typically server or other computing apparatus). The program may be embodied e.g. in a non-transitory carrier medium such as a memory card to implement a computer program product. The program may be adapted, when run on the host, to execute various tasks described herein including e.g. data reception (e.g. health-related data, profile data, etc.), processing including user (profile) matching and creation of predictive data, and data transmission.

Yet, the arrangement may store and utilize environmental data such as temporospatial weather data, (air) pollution such as particulate data, pollen data, and/or data related to pulmonary infections. The environmental data may be of forecast type and/or indicative of a detected current environmental situation, for instance. Detected or predicted current or future presence of an environmental condition such as pollen may thus be indicated in the environmental data concerning at least one location. Accordingly, an indicated, location-related environmental condition may be associated, by the arrangement, to e.g. symptoms reported by user(s) (e.g. aforesaid first user(s)) from the location.

In various embodiments, received data such as environmental data is preferably further utilized e.g. in the creation of the predictive data. For example, a received indication of current or future environmental condition at a location may be used in determining (e.g. through spatial, temporal, or temporospatial interpolation or extrapolation) the likelihood of a user (e.g. aforesaid second user(s)) suffering from the symptoms associated with the condition at the same, near-by or more remote location either immediately or later, based on which a notification or specifically a recommendation may be transmitted to the user.

The terms first and second user device refer herein to how specific data is transferred in an arrangement. A first user device is a user device from which data is received that is used to generate predictive data, while a second user device is a user device which the predictive data is related to.

"Time" may here refer to a specific time or a time interval that may include a specific time as already alluded to hereinbefore. "Location" may here refer to a substantially exact location defined by e.g. coordinates, or an area or region, such as a state or country, county, city or a smaller subarea, such as district, block or e.g. cell tower coverage area of a wireless network whereto a user device may be connected, or an area comprising an exact location.

A "user" of a user device refers here to a preferably person type user that may e.g. be associated with a user account that may be provided through an application, which may be installed on a user device, for example. Thus, a "user" may refer in this context to a user that is at a particular instance signed in to an application that may be provided to be used through a user device.

Health conditions that are discussed in the exemplary embodiments of the invention presented herein are related to asthma and COPD but, as may be appreciated by a person skilled in the art, also other health conditions may be considered.

The exemplary embodiments presented in this text are not to be interpreted to pose limitations to the applicability of the appended claims. The verb "to comprise" is used in this text as an open limitation that does not exclude the existence of unrecited features. The features recited in depending claims are mutually freely combinable unless otherwise explicitly stated.

The novel features which are considered as characteristic of the invention are set forth in particular in the appended claims. The invention itself, however, both as to its construction and its method of operation, together with additional objects and advantages thereof, will be best understood from the following description of specific example embodiments when read in connection with the accompanying drawings.

The previously presented considerations concerning the various embodiments of the arrangement may be flexibly applied to the embodiments of the method mutatis mutandis, and vice versa, as being appreciated by a skilled person.

BRIEF DESCRIPTION OF THE DRAWINGS

Next the invention will be described in greater detail with reference to exemplary embodiments in accordance with the accompanying drawings, in which.

DETAILED DESCRIPTION

Figure 1:
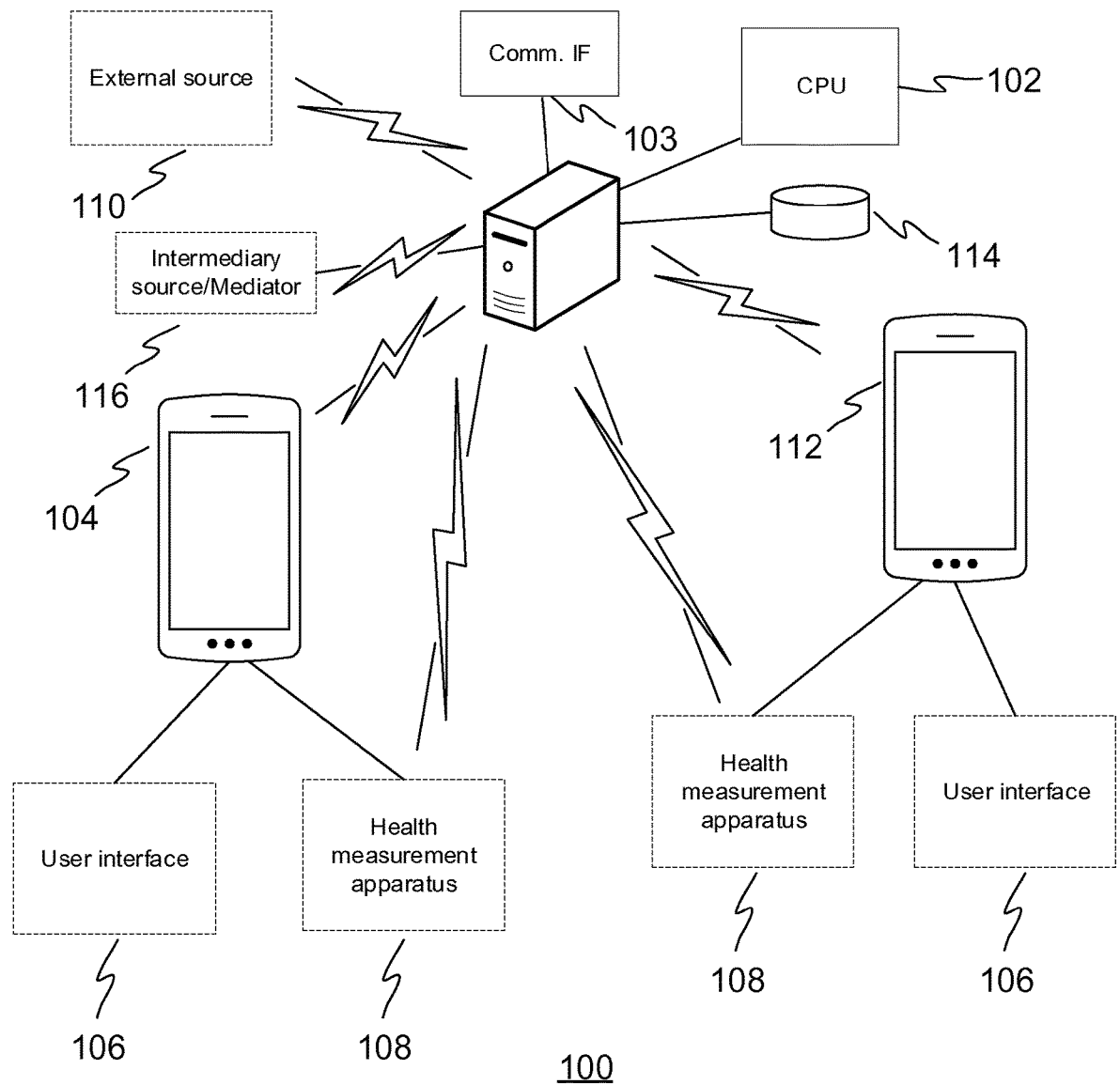
FIG. 1 illustrates an exemplary arrangement according to one embodiment of the invention.

FIG. 1 gives an exemplary arrangement 100 according to an embodiment of the invention. The arrangement 100 may at least comprise e.g. one or more processor-equipped server devices, or alike, accessible via a communication network such as the internet. Additionally, the arrangement 100 may comprise a number of user devices 104, 112 associated with respective users.

Accordingly, health-related data is received by a processor 102 from a first user device 104. The data may be received through an applicable communication medium such as the internet. For communication, the arrangement 100 may comprise one or more communication interfaces 103, which may herein refer to e.g. wireless and/or wired transmitters, receivers, or transceivers operable in a target communication infrastructure such as wired or wireless network. The communication interface 103 may comply with a selected WLAN (wireless local area network), LAN such as Ethernet, and/or cellular standard. Via the communication interface the arrangement 100 may be connected to and accessible via the internet. Such elements may be included in the devices belonging to or at least communicating with the arrangement 100 incorporating e.g. server(s) and user devices.

The processor 102 may, in addition to at least one on-board processing unit (e.g. microprocessor, microcontroller, or a signal processor), i.e. unit hosted by the arrangement incorporating e.g. at least one server itself, refer to at least one remote processor which may be accessed through cloud computing, and/or the processor 102 may refer to at least one virtual processor comprised in a plurality of locations which may be configured to execute procedures presented herein through parallel processing means.

At least some of the health-related data may be received through the use of a user interface (UI) 106. At least some of the data may involve input from a user of the first user device 104. In other embodiments, the data may be automatically transmitted through a user device 104. The UI 106 is preferably established by and/or accessible via user devices 104, 112, and may refer to e.g. a native client application running on a user terminal or browser-accessible (web) UI. The UI may be graphical and support e.g. a map display wherein locations are displayed. The communication interface may comprise or implement at least part of the UI, or at least provide a communication medium for the communication activities carried over via the UI as appreciated by a skilled person.

The user devices 104, 112 such as smartphones, tablets, or e.g. personal or wearable (e.g. wristop) computers typically comprise a processor, memory and communication interface such as a transceiver of their own as easily understood by a person skilled in the art.

The health-related data may be associated with a first time and a first location as contemplated hereinbefore. The first time and the first location may be a time and a location of the first user device 104 at the time that the data is recorded, sent, and/or received by the arrangement, for instance. One or more user devices 104, 112 may be configured to transmit indication of the location to the arrangement based on user input or e.g. automatically according to a predefined or user-defined schedule or based on an occurrence of some other defined triggering condition, for example. An indication of the time may be explicitly included in the transmitted data. In some embodiments, the arrangement may deem the time of receiving the health-related data the time to be associated with the health-related data and location for prediction purposes. Accordingly, the arrangement 100, such as a server computer thereof, may be configured to store an indication of the receive time e.g. as a timestamp in connection with the stored health-related data.

Alternatively or additionally, a different time and/or location may be preferably selected e.g. through the user interface 106 for instance if the health-related data that is sent is associated, e.g. in terms of data recording time and/or recording location, with a different time and/or location than that when the data is sent.

In more detail, temporal data and location data may be in some embodiments obtained through the first user device 104 e.g. through a (master) clock or sensors comprised in the first user device 104, such as a GPS, Glonass or other (satellite) positioning sensor. Alternatively or additionally, temporal data and location data may be received through the first user device 104 through manual inputs through e.g. a user interface 106 by a user of the first user device 104. In some embodiments, also network based positioning (e.g. triangulation or cell identification based) may be utilized. Further, digital device address such as IP address may be utilized in providing at least a coarse estimate of device and related user location.

The health-related data received from the first user device 104 may be data that is related to and indicates a health condition of a user of the first user device 104. The data may for instance comprise data that may indicate the state of a health condition, such as an indicator of the severity of a health condition or a symptom. The data may comprise data that is obtained through self-assessment of the user. For example, the data may comprise a self-assessed value e.g. on a scale that may be indicative of the severity of a health condition or a symptom related to a health condition.

The health-related data may additionally or alternatively comprise data that has been obtained through a measurement of a health condition or measurement of an indicator of a health condition. The aforementioned measurement data regarding a user may be received as manual inputs by the user through a user interface 106 of the first user device 104, and/or may be obtained through an intermediary source 116, and/or or they may be received through a health measurement apparatus 108.

In case health-related measurement data or other health-related data regarding a user of user device 104 may be obtained via an intermediary source 116, the intermediary source 116 may be or comprise e.g. a network-accessible database comprising the data, the arrangement 100 having access to or receiving said data from. The intermediary source 116, or "mediator", may for instance comprise and execute by at least one processor a software application that is configured to obtain and store measurement data from or via an external health measurement apparatus that has been provided by a third party, for example.

In some embodiments, the intermediary source 116 may include the external health measurement apparatus, which may instead of providing data to e.g. a database communicating with the arrangement 100, communicate more directly with the arrangement 100 and transmit data to it e.g. periodically or based on a selected other transmission trigger condition, or responsive to queries by the arrangement 100.

The external health measurement apparatus may comprise e.g. a heart rate/heart rate variability monitor, an activity/step counter or monitor, blood pressure monitor etc. Accordingly, the data provided by it may include e.g. heart rate data (e.g. current, average, max, range, min, etc.), (physical) activity data such as step data (e.g. step count) or distance data such as distance traveled, blood related data such as blood pressure data or blood oxygen saturation, and/or data indicative of e.g. fractional nitric oxide (NO) concentration in exhaled breath (FeNO).

The intermediary source 116 may comprise an electronic system, such as network-accessible digital online service or similar server arrangement, which is associated with the external health measurement apparatus and/or it may be a system that is used for instance by a health care provider or other entity to record data given by an external health measurement apparatus or measurement system. An arrangement 100 may be configured to obtain access to said data automatically (automated transfers occurring e.g. periodically and/or upon changes, wherein the arrangement may be configured to request or fetch such data from the intermediary source, or the source may be configured to send it according to a selected transfer scheme) and/or the data may be received as manual input or as manually triggered from a user of the arrangement 100.

In some embodiments, a user device 104 may be provided with software that connects with remote intermediary source 116 and receives health-related (measurement) data therefrom, whereupon the device 104 may be configured to forward such data to the arrangement 100. In some embodiments, the intermediary source 116 may comprise an air quality or characteristics meter that is configured to measure e.g. particle data such as particle count, VOC values (volatile organic compound), air pressure, temperature, humidity, etc. The air quality meter or other device included in or providing data to the intermediary source 116 may optionally be personal (user-specific). Accordingly, data provided by the source 116 may include user-specific data, optionally substantially exclusively.

At least one health measurement apparatus 108 may in some embodiments be comprised in a user device 104 as optionally removably connectable element(s), if not being practically fixedly integrated therewith, or it may be coupled to a user device 104 e.g. wirelessly or wiredly. The coupling may be physical or it may be executed e.g. through a wireless connection.

A health measurement apparatus 108 may alternatively or additionally to comprising means for communicating with a user device 104 in the possession of a user comprise means for more direct communication with the (remote) arrangement such as processor 102, optionally through a wireless or wired connection (e.g. internet).

In the case of asthma and/or COPD, the health condition measurements that may be executed through a health measurement apparatus 108 may be related to pulmonary function testing.

In embodiments where an arrangement 100 or at least user device 104 connected thereto comprises or is connected with a health measurement apparatus 108, the health measurement apparatus 108 may be for example a peak flow meter or a spirometer, configured to output related data for inclusion in the health-related data, specifically measurement data. Also other health measurement apparatuses 108 may be utilized depending on the embodiment and the health condition involved.

Other health measurement apparatuses 108 that may be utilized may comprise e.g. apparatuses for measurement of blood pressure, blood oxygen saturation, and/or measurement of fractional nitric oxide (NO) concentration in exhaled breath (FeNO), for example.

An arrangement 100 may comprise and/or be at least functionally connected to a plurality of health measurement apparatuses 108. A plurality of health measurement apparatuses 108 may also be related to the same user device 104 or a user account associated with the user device 104, and thus collect data regarding the same user In some embodiments, a processor 102 may also receive other data from one or more sensors and/or detectors comprised in a first user device 104 or sensors and/or detectors that a first user device 104 has access to in terms of e.g. functional (data) connection. For instance, a sensor may include a camera or a temperature sensor and a detector may be a particle detector.

In various embodiments of the invention, also additional data may be received by the processor 102 from a first user device 104 and/or a second user device 112. The additional data may be data that may be utilized to generate a user profile or generally user data that may be associated with a user of a user device 104, 112. The additional data may e.g. comprise information on a user's allergies, other information related to one or more health conditions, and/or information on other characteristics of a user, such as age and/or gender etc. as already discussed hereinearlier.

A user profile may be at least partially generated or completed/supplemented by utilizing the obtained health-related data, e.g. measurement data, that is obtained by the arrangement 100. The health-related data may comprise data from a plurality of sources, such as that obtained via a health measurement apparatus 108 or data obtained via an intermediary source 116 comprising data that has been obtained via an external health measurement apparatus.

Through obtaining various data to be used/stored e.g. in user profiles, matching or comparison of user profiles to each other may be made easier and/or more efficient. Correlations between data may be used to make more efficient predictions.

Any or all data received and/or generated by a processor 102 may be stored in at least one database 114 or other memory structure that is hosted by the device including also the processor 102 or the processor 102 may have access to such database 114 by e.g. wireless or wired communication means.

The arrangement 100 may also receive desired external data from one or more external sources 110. The external data may be received through wireless or wired communication means, for example. The external data source 110 may be a weather service provider or e.g. a database or website that may be maintained by a provider such as a weather service provider. The external data may comprise environmental data, such as data related to weather, allergens, or particulates, for example. The external data may also have temporospatial nature, i.e. it may represent e.g. measurement or prediction data having regard to selected characteristics such as pollen count at a certain location at a certain time. As alluded to above, the data provided by the external source 110 may include or potentially exclusively contain data pertinent to multiple users (e.g. population in an area) and/or other data is not exclusively linked to any single user anyway.

In one embodiment, an additional external source 110 may be a healthcare provider or other instance that may provide external data related to a health condition. The external data related to a health condition may e.g. involve and include statistics that may be utilized to correlate e.g. environmental data with the risk of a health-related exacerbation.

In one embodiment, an external source 110 may be e.g. a source that provides health-related data, e.g. condition and/or symptom data. The external source 110 may for instance be an external service that obtains symptom data from a plurality of users. The symptom data, such as pollen related symptom data, may be used to e.g. create new user profiles or correlate symptoms with environmental or other data. Accordingly, e.g. more accurate or complete predictions may be established.

A user profile may in some embodiments comprise genetic data. Genetic data may be used for matching or comparing user profiles with each other.

Genetic data may be utilized in some embodiments of an arrangement 100 in the generation of predictive data. Genetic data may, for instance, provide information on how a user may react to an environmental condition or how his/her health may evolve. Genetic data may be obtained via an external source 110 or an intermediary source 116 and/or via a measurement apparatus/kit provided by the provider of the arrangement 100. The genetic data (or any other data obtained by the arrangement 100) may then considered to be health-related data, supplementary data, or external data etc. depending on the source of the data. The data may be used for profile supplementation and/or the generation of predictive data.

Various considerations described above relative to a first user or first user device 104 are naturally applicable to a second user or related second user device 112 as well, having regard to e.g. external 110 and intermediary 116 sources, health measurement apparatuses 108, sensors, and related data obtained and utilized.

Utilizing the received data, a processor 102 is configured to generate predictive data that may be associated with a second time and a second location. The second time and second location may be associated with a second user device 112 and/or a user of the second user device 112 (being different user than the user of device 104) and/or technically, e.g. a user account or profile associated with a user of the second user device 112.

For instance, health-related data received through the first user device 104 may indicate that an associated first user has experienced a worsening in a health condition or symptom e.g. related to breathing that is associated with a first time and a first location. Additional data may also have been received that indicates that said first user is susceptible to some environmental condition that may affect his/her health, such as that he/she may be allergic to birch. External data may have been received that may be indicative of weather conditions, such as predictions involving wind, temperature and/or humidity. External data may also comprise information regarding birch pollen and/or in some embodiments information regarding environmental conditions such as pollen may be received through one or more sensors comprised in the first user device 104.

Utilizing the received data in this exemplary scenario, a processor 102 may thus generate predictive data that may indicate that a user of a second user device 112, hereinafter second user, who may also be allergic to birch may experience a change in his/her health at a second time and/or a second location. The second location may be a current location of a second user device 112 as determined by any applicable positioning technique as discussed hereinelsewhere, for example, or a location that has been specified by a user of a second user device 112. Nevertheless, the arrangement 100 preferably obtains location data indicative of the second location associated with the second user device 112/second user. The second location may also be a location that the second user device 112 may reside at a future time based on an executed location estimation procedure (utilizing e.g. past locations and a selected extrapolation technique, and/or calendar or other more or less implicit location data such as travel (ticket) data available and possibly provided by a user device 112).

Generally, in various embodiments the data such as health-related data used for generating the predictive data regarding the second user may be selected from all available data and/or weighted based on user profile matching wherein a number of first user(s) that correlate well enough according to a selected criterion, such as common health condition (e.g. allergy) and/or similar demographic data, are selected or given more weight in the prediction.

The predictive data may comprise information that may be related to a symptom and may additionally in some cases be indicative of the severity of said symptom.

The predictive data may for instance, in the aforementioned example concerning birch allergies, through user profile data and/or data from one or more external sources 110, predict the type of symptom and possibly a severity of the symptom that may be experienced by a user of the second user device 112. The utilized data may in this example comprise a level of birch pollen and how this level of pollen may affect a user of a second user device 112 based on data such as historical data retrieved from a user profile and/or other user profiles with similarities and/or statistical data concerning users with a similar patient/user profile.

The selected prediction technique may include interpolation and/or extrapolation (e.g. linear or polynomial) of the utilized data, for example. E.g., from the obtained datapoints indicating certain symptoms recorded by/regarding a number of first users suffering from a certain medical condition, the symptoms recorded as taking place in certain places at certain times, future locations and related times could be estimated for experiencing the same or at least similar symptoms by at least one second user if suffering from the same or similar medical condition such as allergy with the number of first users. Respectively, locations/times with a reduced risk of experiencing the symptoms may be determined.

In some embodiments, based on the predictive data, a notification (message), such as an "alert" or "warning" in applicable cases, may be sent or triggered by the arrangement 100 to the second user via the second user device 112. A notification may e.g. mean that the second user is notified through a user interface 106 of information that may concern his/her health or be relevant to the user or their health.

A notification may mean that the predictive data itself is sent to a second user device 112 or that other information that has been generated based on the predictive data is sent to a second user device 112.

A notification may be sent for instance if the predictive data indicates that a user of the second user device 112 may experience a symptom. Alternatively or additionally, a notification may be sent e.g. if the predictive data indicated that the severity of a symptom exceeds a certain threshold. Alternatively or additionally, a notification may be sent if a certain threshold is exceeded regarding an environmental trigger that may trigger a symptom, such as if a level of pollen has exceeded a certain threshold.

A notification may comprise e.g. data relating to a symptom and/or data relating to a cause of a symptom. A notification may comprise information indicating that a possibility of an event related to a health condition may occur. In general, a notification may be indicative of a change in the health status of the user of the second user device 112. Alternatively or additionally, the condition affecting the health status, e.g. the presence of birch pollen and/or its level in the example discussed herein, may be comprised in a notification.

Certainly, in some embodiments the notifications may also be purely informative or e.g. positive in a sense that they indicate a situation wherein the health status of the user is going to substantially remain as is or even enhance having regard to the concerned location and time.

In an embodiment, a user of the second user device 112 may confirm or qualify the validity of predictive data. This may be done for example by providing, through the user interface 106, means for indicating if e.g. a symptom has occurred that has been predicted by the predictive data. It may also be possible to indicate an extent to which predictive data has been valid. The validity of predictive data may be utilized if predictive data concerning similar conditions is generated in the future and/or it may be utilized to modify a user profile. A selected prediction model may be updated, or specifically adapted, based on the obtained user feedback.

Based on the predictive data, the arrangement 100 may further generate one or more recommendations that may be sent to a second user device 112. The recommendations may e.g. refer to actions that may be taken by the associated user in order to reduce the probability or severity of e.g. a symptom that has been predicted to take place. The recommendations may for instance suggest that a user of the second user device 112 stays indoors, changes location/ moves to a suggested location and/or the recommendations may be related to medications. Recommendations may also be considered to be part of the generated predictive data.

The effectivity of actions that have been taken in response to recommendations may also be recorded by an arrangement 100 and this data may be utilized in generation of future recommendations and/or it may be used to modify a user profile.

Future recommendations and/or updated/improved generation of predictive data based on feedback/received data indicating outcome of user action or response to environmental conditions may be generated and provided for a user by using data related to him/herself and/or using data related to another user with a sufficiently similar (according to selected criteria) profile. "Similar" profile may again refer to a user that has been matched with another user by comparison of the user profile data, and the compared/matched data that is considered may differ in different cases.

A user profile may also be modified through first receiving health-related data and/or additional data from a user device 104, 112, and then comparing this data to health-related data and/or additional data received from another user device 104, 112 and/or data from one or more external sources such as a healthcare provider. For instance, data from a user device 104, 112 may indicate that a user having a user profile that does not indicate an allergy to birch pollen experiences symptoms that correlate with other users/patients that do suffer from birch allergy. Received data from the user device 104, 112 may be e.g. self-assessed symptoms and/or data from one or more health measurement apparatuses 108 and environmental data regarding e.g. pollen may be received from one or more external sources. Comparison may indicate statistically that other users that have an indication of a birch allergy in their user profile usually experience similar symptoms and/or changes in health status (possibly related to measurements by a health apparatus) in the presence of certain environmental data such as birch pollen. The user profile may then be updated to indicate that the user/patient has developed an allergy to birch, for instance.

In an embodiment, it may be possible for a user of a second user device 112 to indicate a location where he/she may reside at a future time. An arrangement 100 may then generate predictive data regarding that time and location and inform a user of the second user device 112 of the predictive data. Also recommendations may be given. Thus, a user of the second user device 112 may prepare himself/herself for possible future conditions at a certain location and e.g. take appropriate medication with him/her or change plans and not travel to a certain location.

In some embodiments, the arrangement 100 may be configured to send data to an external source 110, such as a healthcare provider. Data may be sent automatically or the sending may be actuated or at least accepted through a user of a user device 104, 112. For instance, a doctor may thus be able to keep track of the status of a health condition of his/her patient through the arrangement 100.

In an embodiment of the present invention, the health-related data or additional data may comprise information related to medication. For example, the arrangement 100 may receive data that indicates a dosage for a certain medication that a user uses for a particular symptom. Using this data and/or data received through other user devices 104, 112 and/or data from external sources 110, an arrangement 100 may in conjunction with generating predictive data, also predict medication to be used and possibly a dosage or dosing frequency that should be applied. Data related to medication may be communicated to a user in recommendations that may be given associated with the predictive data.

An arrangement 100 may be configured to obtain and store user feedback also regarding implications of predictive data. For example, predictive data may indicate certain environmental conditions that may lead to symptoms for a certain user. The predictive data may be provided to the user and the user may, as feedback to the predictive data, provide information on e.g. a dose of medication that he/she has been required to take in response to the predictive data. Such feedback data may then be used to predict required medication doses in various future scenarios where similar data is obtained or similar predictive data is generated.

In some embodiments, user feedback and/or other information, such as user specific access records regarding the (predictive data provided by the) arrangement or e.g. transmission or viewing records of predictive data, and/or detected user activity in using the arrangement or related client application, may be utilized in determining or estimating whether the user has accessed or seen the predictive data and/or acted based thereupon. Outcome of this determination or estimation may, in turn, be configured to adapt the generation of predictive data such as update of a used prediction model.

For example, if the predictive data indicates an increased risk associated with a certain health condition at a certain location at a certain instant due to e.g. worsening environmental conditions (allergens, particulates, weather, etc.), a user may, after having accessed such predictive information, take responsive actions or, in practice, omit performing previously intended actions, which may refer to avoiding high-risk areas, staying inside instead of going out, omit physical exercise, etc. These actions or generally change in behavior also affect the data (provide e.g. bias therein) that may be provided by the user to the arrangement for various purposes such as determination of predictive data for the future, for other users, etc.

Indeed, if the users proactively change their behavior to minimize the detrimental effect of a predicted phenomenon as indicated by the predictive data, also their symptoms may be reduced in contrast to a "normal" situation, i.e. situation where the predictive data with potential recommendations was unavailable. Accordingly, data weighting may be dynamically applied by the arrangement, optionally putting some de-emphasis on the health-related data obtained from users that have relied upon or have at least been deemed to rely upon predictive data previously provided to them, among other possibilities.

In various embodiments, feedback data may be used to predict medication needs and in this case a user may for instance be warned in advance by the arrangement when he/she will be needing medication and/or the user may be reminded to take medication with them. The arrangement 100 may in some embodiments have access to prescription data of a user and may be configured to remind a user of e.g. how much medication he/she has left and/or renew a prescription automatically through available communication connections.

In some embodiments where medication needs are predicted, the information may indicate predicted medication needs relating to a location. This information may be sent to an external source 110 such as an organization, pharmacy, and/or a wholesale pharmaceutical business, in which case increasing medication needs may be taken into account e.g. in the production, logistics, orders, etc. of the medication.

Generated predictive data and data obtained from an external source 110 may be flexibly combined in a variety of ways. For example, an external source 110 may comprise a hospital or other health care provider, and it may be determined that certain environmental conditions lead to or generally correlate with doctor or hospital visits of certain patients. This data may be used to predict doctor or hospital visits in future cases where similar data is received or similar conditions are predicted. An external source 110 may then be informed of e.g. increasing health care needs, such as increasing hospital visits.

In some embodiments, the health-related data, additional data, and/or external data may comprise data related to pulmonary infections. In this case, the data related to pulmonary infections may be regarded as environmental data that may affect the health condition of a user of a second user device 112. An arrangement 100 may then send a notification to a second user device 112 e.g. if predictive data indicates that a user of the second user device 112 will be susceptible to an infection at a certain location at a future time.

In yet further embodiments, an arrangement 100 may make generated predictive data available for external users who are not users of user devices 104, 112. For instance, an arrangement may generate predictive data that concerns a certain health condition, such as an allergy. The predictive data may then be made available to external users for instance via a web page or other digital media so that external users suffering from the allergy may obtain the predictive data without having to provide their own health-related data to the arrangement 100, for example.

Figure 2:
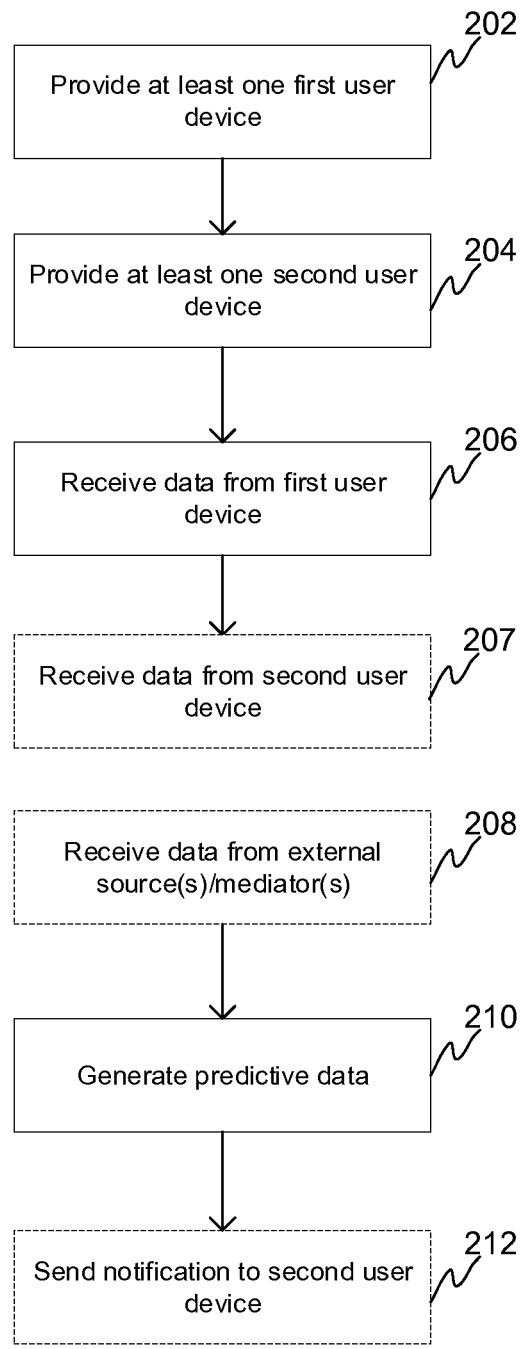
FIG. 2 illustrates steps that may be performed in a method according to an embodiment of the invention.

FIG. 2 shows items of a method according to an embodiment of the present invention. At 202, at least one first user device 104 is provided while in 204, at least one second user device 112 is provided. The user devices 104, 112 may be specifically manufactured for use with the present invention or they may be general purpose user devices such as ordinary smartphones, tablets or computers (laptop, desktop, wearable, etc.) configured to communicate with the remote parts of the arrangement 100, such as a remote server. For communication and e.g. user interaction purposes a user device may include e.g. a wireless or wired transceiver and necessary software (e.g. dedicated application or generic browser) run by a processor (a "processor" may herein refer to one or more at least functionally connected processing units) and stored in a memory of the user device.

In step 206, data such as user data, specifically e.g. health-related data is obtained, being typically received at least from the at least one first user device 104, wherein the data is associated with a first time and a first location as well as naturally with the user of the at least one user device 104. For example, the data may be associated with the location of the first user device/first user at the time when the data is received. The health-related data may for instance indicate the occurrence of a symptom and possibly its severity. Time and location data may be included in the data received from the at least one first user device 104 and/or obtained from other sources if not generated internally by the arrangement (e.g. time of receipt could be utilized as the first time as mentioned above).

At 207, data from the second user device 112 or at least regarding the second user device 112 and/or second user (user of the second user device 112) may be received, including e.g. location data.

Generally, further user data such as user profile data or other user data discussed hereinbefore may be obtained in connection with steps 206, 207, and/or 208, or at separate step(s) not shown in the fig. in favor of clarity.

External data from at least one external source and/or intermediary source may be received in 208. This data may be related to environmental conditions such as weather conditions and possibly data related to particulates or pollen. The data may include temporospatial data as discussed hereinbefore.

At 210, the received data is utilized to generate predictive data that may be related to the at least one second user device 112/second user. The predictive data may be associated with a second time and a second location which may be related to the second user device 112.

Preferably, in 212 a notification may be sent to a second user device 112. The sending may be executed when at least one criterion is met, such as the predictive data being indicative of a sufficient change in the health status of the user of the second user device 112, for instance if a symptom exceeding a threshold in severity is predicted.

Although in this example, the second user device 112/second user was a recipient of the predictive data, or basically thus a user of the predictive data in favor of his/her health condition, a person skilled in the will easily comprehend the fact that in various fully applicable embodiments and from the standpoint of other user devices (e.g. device 104)/other users, the second user device 112/second user may further serve as a source of health-related data utilized for the generation of predictive data to be provided to the other user devices/other users.

The invention has been explained above with reference to the aforementioned embodiments, and several advantages of the invention have been demonstrated. It is clear that the invention is not only restricted to these embodiments, but comprises all possible embodiments within the spirit and scope of inventive thought and the following patent claims.

The features recited in dependent claims are mutually freely combinable unless otherwise explicitly stated.

The invention claimed is:

1. An arrangement for prediction of health condition related data, wherein the arrangement comprises at least one communication interface configured to receive first health-related data, comprising measurement data, from at least one first user device of at least one first user, associated with a first time and a first location and at least one processor, wherein the at least one processor is configured to utilize first additional data received from the at least one first user device to generate user profile data for the at least one first user, the first additional data comprising information related to one or more health conditions of the at least one first user, wherein the at least one processor is additionally configured to receive temporospatial environmental data from at least one external source, said temporospatial environmental data comprising weather data, air pollution data, allergen data, particulate data, and/or data related to pulmonary infections, and further utilize said received first health-related data, temporospatial environmental data, and first additional data to generate predictive data to be indicated to a second user device of a second user and associated with a second time and a second location, based on comparison or matching of second additional data and/or second health-related data associated with the second user with corresponding additional data and/or corresponding health-related data associated with a plurality of other users comprising said at least one first user and determining that the at least one first user is a user whose user profile data matches user profile data or the second health-related data of the second user and is to be utilized for generating the predictive data, wherein if the first health-related data indicates that the at least one first user has experienced a worsening in health condition that is associated with the first time and first location, the predictive data indicates an increased risk associated in health condition of the second user if worsening environmental conditions are determined.

2. The arrangement of claim 1, wherein the arrangement additionally comprises at least one health measurement apparatus, integral with or at least functionally connected to said at least one first user device, configured to take a respiratory measurement.

3. The arrangement of claim 2, wherein said first health-related data comprises measurement data provided by the health measurement apparatus.

4. The arrangement of claim 1, wherein the processor is configured to send a notification to the second user device based on said predictive data if one or more predefined criteria are met.

5. The arrangement of claim 4, wherein the notification is indicative of a predicted future change in the health status of the second user of the second user device.

6. The arrangement of claim 1, wherein the processor is configured to utilize demographics data and/or medical records or diagnosis data indicative of a medical condition or disease, associated with the at least one first user and the second user and received from the at least one first user device and the second user device, respectively, to generate the predictive data.

7. The arrangement of claim 1, wherein the at least one processor is additionally configured to send recommendations regarding actions to be taken related to a health condition.

8. A method for prediction of health condition related data to be performed by an electronic arrangement comprising at least one computing device, wherein the method comprises:
receiving first health-related data from at least one first user device, associated with a first time and a first location,
generating user profile data for at least one first user utilizing first additional data received from the at least one first user device, the first additional data comprising information related to one or more health conditions of the at least one first user,
receiving temporospatial environmental data from at least one external source, said temporospatial environmental data comprising weather data, air pollution data, allergen data, particulate data, and/or data related to pulmonary infections,
matching second additional data and/or second health-related data associated with the second user with corresponding additional data and/or corresponding health-related data associated with a plurality of other users comprising said at least one first user and determining that the at least one first user is a user whose user profile data matches the user profile data or the second health-related data of the second user, and
generating predictive data related to at least one second user device and associated with a second time and a second location, based on said first health-related data, temporospatial environmental data, first additional data, and said matching, the predictive data indicating an increased risk associated in health condition of the second user if worsening environmental conditions are determined and if the health-related data indicates that the at least one first user has experienced a worsening in health condition that is associated with the first time and first location.

9. A non-transitory carrier medium comprising a computer-executable instruction program configured, when executed by at least one processor, to perform:
receiving first health-related data from at least one first user device, associated with a first time and a first location,
generating user profile data for at least one first user utilizing first additional data received from the at least one first user device, the first additional data comprising information related to one or more health conditions of the at least one first user,
receiving temporospatial environmental data from at least one external source, said temporospatial environmental data comprising weather data, air pollution data, allergen data, particulate data, and/or data related to pulmonary infections,
matching second additional data and/or second health-related data associated with the second user with corresponding additional data and/or corresponding health-related data associated with a plurality of other users comprising said at least one first user and determining that the at least one first user is a user whose user profile data matches the user profile data or the second health-related data of the second user, and
generating predictive data related to at least one second user device and associated with a second time and a second location, based on said first health-related data, temporospatial environmental data, first additional data, and said matching, the predictive data indicating an increased risk associated in health condition of the second user if worsening environmental conditions are determined and if the health-related data indicates that the at least one first user has experienced a worsening in health condition that is associated with the first time and first location.

* * * * *